United States Patent
Kawasaki (10) Patent No.: US 9,939,371 B2
(45) Date of Patent: Apr. 10, 2018

(54) SYSTEMS AND METHODS FOR MULTI-COMPONENT DETECTION

(71) Applicant: Empire Technology Development LLC, Wilmington, DE (US)

(72) Inventor: Takayoshi Kawasaki, Kyoto (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 55 days.

(21) Appl. No.: 15/012,585

(22) Filed: Feb. 1, 2016

(65) Prior Publication Data

US 2017/0219483 A1 Aug. 3, 2017

(51) Int. Cl.
*G01N 21/00* (2006.01)
*G01N 21/27* (2006.01)

(52) U.S. Cl.
CPC ....... *G01N 21/27* (2013.01); *G01N 2201/062* (2013.01); *G01N 2201/068* (2013.01)

(58) Field of Classification Search
CPC ......... G01N 2800/304; G01N 2800/52; G01N 2800/60; G01N 33/6893; G01N 15/0606; G01N 15/0656; G01N 2015/0065; G01N 21/6428; G01N 21/6454; G01N 21/648; G01N 27/3272; G01N 27/3274; G01N 33/6848

See application file for complete search history.

(56) References Cited

U.S. PATENT DOCUMENTS

| 5,726,805 A | 3/1998 | Kaushik et al. |
| 2005/0014179 A1* | 1/2005 | Karlsson ............. G01N 33/543 435/6.1 |

(Continued)

FOREIGN PATENT DOCUMENTS

| JP | 2009-150904 | 7/2009 |
| JP | 2011-111660 | 6/2011 |

OTHER PUBLICATIONS

Akihiro, S., "Strange relationship inkjet and digital camera, the resolution," accessed at http://web.archive.org/web/20131110072825/http://itpro.nikkeibp.co.jp/article/OPINION/20070626/275862/, Jun. 28, 2007, pp. 1-3.

(Continued)

*Primary Examiner* — Michael P Stafira
(74) *Attorney, Agent, or Firm* — Moritt Hock & Hamroff LLP; Steven S. Rubin, Esq.

(57) ABSTRACT

A detection system for detecting analytes in a sample, and methods of making and using the detection system, are disclosed. The detection system includes at least one sensor having a substrate and an optical interference layer on the substrate. The optical interference layer includes a plurality of sample segments, wherein two or more of the plurality of sample segments are configured to have different affinities to two or more analytes in the sample. The detection system further includes at least one light source configured to illuminate the two or more of the plurality of sample segments, and at least one image detector configured to detect an interference spectrum from each of the two or more of the plurality of sample segments illuminated by the light source, thereby detecting the two or more analytes in the sample.

21 Claims, 8 Drawing Sheets

(56) References Cited

U.S. PATENT DOCUMENTS

2012/0150005 A1* 6/2012 Hoss .................. A61B 5/14532
600/347
2014/0249055 A1* 9/2014 Yamada ............... G01N 21/253
506/12

OTHER PUBLICATIONS

Albert, K.J., "Cross-Reactive Chemical Sensor Arrays," Chem Rev., vol. 100, No. 7, pp. 2595-2626 (Jun. 24, 2000).
Gawalt, E. S., et al., "Self-Assembly and Bonding of Alkanephosphonic Acids on the Native Oxide Surface of Titanium," Langmuir, vol. 17, No. 19, pp. 5736-5738 (Aug. 18, 2001).
Kawasaki, T., et al., "Laser Response of a Quartz Crystal Microbalance: Frequency Changes Induced by Light Irradiation in the Air Phase," Analytical Sciences, vol. 25, pp. 1069-1075, The Japan Society for Analytical Chemistry (2009).
Lee, S. W., et al., "Molecular Imprinting of Azobenzene Carboxylic Acid on a TiO2 Ultrathin Film by the Surface Sol-Gel Process," Langmuir, vol. 14, No. 10, pp. 2857-2863 (1998).
Zhang, W. D., and Zhang, W-H., "Carbon Nanotubes as Active Components for Gas Sensors," Journal of Sensors, vol. 2009, pp. 16 (2009).

* cited by examiner

SYSTEMS AND METHODS FOR MULTI-COMPONENT DETECTION

BACKGROUND

The detection, analysis and monitoring of biological analytes (such as polypeptides, polynucleotides, polysaccharides and the like) or environmental analytes (such as pesticides, biowarfare agents, food contaminants and the like) have become increasingly important for research and industrial applications. Conventionally, analyte detection systems are based on analyte-specific binding between an analyte and an analyte-binding receptor. Such systems typically require complex multi-component detection systems, complex electrochemical detection systems, or require that both the analyte and the receptor be labeled to enable detection.

These multi-component systems for detection and analysis of analytes often require an array of various types of sensor elements. For example, some devices involve a crystal oscillator microbalance technology for quantifying substances adsorbed on a surface, and some devices involve the use an array of semiconductor-based sensors to detect the substance. These devices are often expensive and difficult to produce. Therefore, there is a need for sensitive, simple, and less expensive detection devices.

SUMMARY

The present disclosure relates to detection systems for detecting analytes in a sample, and methods of making and using the systems. The detection systems as described herein may rely on reflectometric interference spectroscopy (RIfS) to detect the analytes in the sample.

In some embodiments, a detection system for detecting two or more analytes in a sample comprises:
  at least one sensor comprising:
    a substrate; and
    an optical interference layer on the substrate, the optical interference layer comprising a plurality of sample segments, wherein two or more of the plurality of sample segments are configured to have different affinities to two or more analytes in a sample;
  at least one light source configured to illuminate the two or more of the plurality of sample segments; and
  at least one image detector configured to detect an interference spectrum from each of the two or more of the plurality of sample segments illuminated by the light source, thereby detecting the two or more analytes in the sample.

In some embodiments, a method of detecting two or more analytes in a sample comprises:
  providing a sample suspected of containing two or more analytes to be detected;
  contacting the sample with at least one sensor, the sensor comprising:
    a substrate; and
    an optical interference layer on the substrate, the optical interference layer comprising a plurality of sample segments, wherein two or more of the plurality of sample segments are configured to have different affinities to the two or more analytes;
  illuminating the two or more of the plurality of sample segments with at least one light source; and
  detecting an interference spectrum from each of the two or more of the plurality of sample segments, thereby detecting the two or more analytes in the sample.

In some embodiments, a method of making an optical interference substrate comprises:
  forming an optical interference layer on a substrate;
  segmenting the optical interference layer into a plurality of sample segments; and
  configuring two or more of the plurality of sample segments to have different affinities to two or more analytes.

In some embodiments, a handheld device or a portable device comprises the detection system described herein.

BRIEF DESCRIPTION OF THE DRAWINGS

FIGS. 2A to 2D show non-limiting examples of substrates having different optical interference layers.

FIGS. 4A and 4B show non-limiting examples of detection systems having different image detectors.

FIGS. 5A to 5C show various graphical representations comparing characteristics of reflected light from a titanium dioxide optical interference layer under different conditions.

FIGS. 6A to 6C show various graphical representations comparing characteristics of reflected light from a titanium dioxide optical interference layer under different conditions.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Detection System

Reflectometric Interference Spectroscopy (RIfS) generally relates to detection methods based on interference of light beams at thin interfaces.

In RIfS detection methods, the light source is usually directed onto a multi-layer structure (for example, a substrate having an optical interference layer), which may result in constructive and destructive superposition of partial beams of light reflected from each layer of the multi-layer substrate to form an interference spectrum. The physical thickness and the refractive index of the optical interference layer can determine the characteristics of the interference spectrum. When an analyte interacts with the optical interference layer, the physical thickness and the refractive index of the layer may change to cause a change in characteristics of the interference spectrum (for example, a shift in the spectrum, a change in intensity, a change in reflectance, and/or other characteristics). By monitoring the change in the characteristics of the interference spectrum before and after analyte interaction with the optical interference layer, information about interaction processes between the analyte and the optical interference layer, and hence the type and amount of the analyte, can be obtained.

For example, when an analyte (which generally has a refractive index greater than that of the optical interference layer) is adsorbed on a surface of the optical interference layer, the spectrum associated with the optical interference of reflected light generally shifts. That is, the intensity of reflected light in the longer wavelength range decreases, while the intensity of reflected light in the shorter wavelength range increases. The changes in intensity can be due to an increase in thickness of the optical interference layer after analyte adsorption. The changes in intensity can, for example, be quantified by measuring changes in reflectance of the reflected light, or changes in number of pixels of color components in the reflected light.

Without being limited to any particular theory, it is believed that detection systems described herein rely on the phenomenon that the interference spectrum changes when analytes are adsorbed on the surface of the optical interference layer. The surface of the optical interference layer can be segmented two-dimensionally into an array of sample segments, and the sample segments can be configured differently from one another to exhibit different affinities to different analytes. Different analytes can accordingly exhibit different interaction behaviors on the sample segments. The different interaction behaviors can be quantified by measuring changes in the characteristics of the interference spectrum from each of the sample segments, thus allowing the detection system to be capable of detecting multiple analytes simultaneously. Changes in the characteristics of the interference spectrum can be detected using an image detector. For example, the changes can be measured by taking a difference in reflectance or changes in number of pixels of various color components of the interference spectrum, before and after analyte adsorption at one or more selected wavelengths (for example, at two specific wavelengths). The changes in characteristics of the interference spectrum can be detected for each of the sample segments in the array, thereby allowing simultaneous two-dimensional processing of the interference spectrums from the array of sample segments, and simultaneous detecting multiple analytes.

In addition, the detection system described herein can be incorporated into, for example, a handheld device or a portable detection device to provide a mobile detection system with a high degree of specificity, accuracy and sensitivity.

The detection system as described herein may include at least one sensor. The sensor may include a substrate, and an optical interference layer on the substrate. The optical interference layer may include a plurality of sample segments, wherein two or more of the plurality of sample segments are configured to have different affinities to two or more analytes in a sample. The detection system may further include at least one light source configured to illuminate the two or more of the plurality of sample segments, and at least one image detector configured to detect an interference spectrum from each of the two or more of the plurality of sample segments illuminated by the light source, thereby detecting the two or more analytes in the sample.

The type of light source is not particularly limited. For example, the light source can be a broadband light source. The broadband light source can be a light source that is operable to emit light spanning a range of wavelengths at any given point in time. For example, the broadband light source can be operable to produce broadband light having wavelengths of about 200 nm to about 800 nm. In some examples, the light source can be any light source that is capable of emitting ultraviolet light, visible light, infrared light, or any combination thereof.

The optical interference layer may have a thickness that is in the nanometer range or in the micrometer range. For example, the optical interference layer may have a thickness of about 1 nm to about 100 µm. In further examples, the thickness of the optical interference layer may be about 1 nm, about 5 nm, about 10 nm, about 50 nm, about 75 nm, about 100 nm, about 200 nm, about 250 nm, about 300 nm, about 400 nm, about 500 nm, about 1 µm, about 2 µm, about 5 µm, about 10 µm, about 50 µm, about 100 µm, or a thickness between any of these values.

The substrate can be metallic or non-metallic. In some examples, the substrate includes a metallic material. Examples of suitable metallic materials include titanium (Ti), silicon (Si), aluminum (Al), germanium (Ge), zirconium (Zr), hafnium (Hf), rutherfordium (Rf), chromium (Cr), molybdenum (Mo), tungsten (W), silver (Ag), gold (Au), or any combination thereof. In some embodiments, the metallic material is titanium (Ti). In some examples, the substrate includes an organic material, such as an organic film. Examples of suitable organic materials include a synthetic polymer, a biopolymer, a self-assembled monolayer (SAM) membrane, a bilayer membrane, or any combination thereof. In some examples, the synthetic polymer includes polymethylmethacrylate (PMMA), polymethacrylate (PMA), polycarbonate (PC), polyethylene (PE), polypropylene (PP), polyethylene terephthalate (PET), polyacrylate (PA), or any combination thereof. In some examples, the substrate includes an organometallic complex. Non-limiting examples of the organometallic complex include a coordination complex, a metal-organic framework, or any combination thereof.

The optical interference layer may have a smooth surface, for example, a substantially non-porous surface. The optical interference layer may have a refractive index that can generate an interference spectrum with an intensity effective to enable characteristics of the spectrum to be detected at each sample segment. In some examples, the optical interference layer may have a refractive index of equal to or more than 1.5 for at least one wavelength of light. In some examples, the optical interference layer may have a refractive index of equal to or more than 2 for at least one wavelength of light. In some examples, the optical interference layer may have a refractive index of equal to or more than 1.3 for visible light. In some examples, the optical interference layer may have a refractive index of equal to or more than 1.5 for visible light. In some examples, the optical interference layer may have a refractive index of equal to or more than 2 for visible light. In some examples, the optical interference layer may have a refractive index of equal to or more than 1.5 for infrared light. In some examples, the optical interference layer may have a refractive index of equal to or more than 2 for infrared light. In some examples, the optical interference layer may have a refractive index of equal to or more than 1.5 for ultraviolet light. In some examples, the optical interference layer may have a refractive index of equal to or more than 2 for ultraviolet light. The refractive index of the optical interference layer may be different for different wavelengths of light.

The optical interference layer can also be configured with an increased surface area to enhance sensitivity of detection. For example, the optical interference layer can be porous. The optical interference layer can also include smooth areas interspersed with porous areas.

The optical interference layer can include at least one metal oxide. For example, the optical interference layer can include $TiO_2$, $ZrO_2$, $HfO_2$, $Cr_2O_3$, or any combination thereof. In some examples, the optical interference layer includes $TiO_2$. The optical interference layer can alternatively include at least one polymeric material. For example, the polymeric material can include a polycarbonate. The polymeric material may be porous or may have a smooth surface. The porous polymeric material can have micro-sized and/or nano-sized pores.

The thickness and/or the refractive index of the optical interference layer can be determined based on the desired optical properties of the sensor. For example, the thickness and/or the refractive index of the optical interference layer can be such that light reflecting from each sample segment forms an interference spectrum at an intensity effective for detection by the image detector.

The two or more analytes in the sample may include a first analyte and a second analyte, and at least one of the plurality of sample segments can have an affinity selective to the first analyte. At least another of the plurality of segments can have an affinity selective to the second analyte. The at least one of the plurality of segments and the at least another of the plurality of segments can have different affinities to the first analyte. The at least one of the plurality of segments and the at least another of the plurality of segments can also have different affinities to the second analyte. There can also be one or more additional analytes in the sample, and one or more other of the plurality of sample segments can have affinities selective to the respective one or more additional analytes in the sample. For example, at least another of the plurality of sample segments may have an affinity to a third analyte, at least another of the plurality of sample segments may have an affinity to a fourth analyte, and so on.

In some examples, the two or more analytes can be a small molecule, a protein, a nucleic acid, or any combination thereof. In other examples, at least one of the two or more analytes can be water, alcohol (for example, ethanol), ketone (for example, acetone), alkyl halide (for example, chloroform or dichloromethane), toluene, ether, or any combination thereof. In further examples, at least one of the two or more analytes is an antibody, an antigen, a ligand, a DNA molecule, a RNA molecule, or any combination thereof. In some examples, at least one of the two or more analytes is ethanol. In some examples, at least one of the two or more analytes is acetone. In some examples, at least one of the two or more analytes is water. In some examples, at least one of the two or more analytes is an organic solvent, such as halogenated hydrocarbons, homologous alcohols, ionic compounds, or other organic compounds.

The analytes can be present in either a gaseous sample or a liquid sample. For example, at least one of the two or more analytes may be present in a gaseous sample. In other examples, at least one of the two or more analytes may be present in a liquid sample. In some examples, at least one of the two or more analytes may be ethanol in gas phase. In some examples, at least one of the two or more analytes may be ethanol in liquid phase. In some examples, at least one of the two or more analytes may be acetone in gas phase. In some examples, at least one of the two or more analytes may be acetone in liquid phase.

The sample segments can be configured to have different affinities to different analytes. For example, at least one of the plurality of sample segments can be configured to exhibit a sensitivity and selectivity to a first analyte, and at least another of the plurality of segments can be configured to exhibit a sensitivity and selectivity to a second analyte that is different from the first analyte. The configuring of the sample segments can be achieved through various surface treatment agents. For example, different sample segments, each including a segmented portion of the optical interference layer, can be contacted with different kinds of surface treatment agents at their surfaces to develop different sensitivities and selectivities to different analytes. Non-limiting examples of the surface treatment agents include a carboxylic acid, a phosphoric acid, a bio-polymer, a synthetic polymer, a metal organic compound, or any combination thereof. At least one or more of the sample segments may not require treatment by the surface treatment agent if the analyte to be detected can be selectively adsorbed onto non-treated optical interference layer. For example, ketones such as acetone, alcohols such as methanol and ethanol, aldehydes, and so on, can be adsorbed onto a titanium dioxide optical interference layer without having to treat the surface of the titanium dioxide optical interference layer with a surface treatment agent.

The choice of surface treatment can be dependent on the type of analyte to be detected in the sample. For example, the optical interference layer can be surface treated with a carboxylic acid or phosphoric acid to detect certain inorganic analytes. In another example, the optical interference layer can be immobilized with an antibody to detect antigens. In another example, deoxyribonucleic acid (DNA), configured to detect DNA or ribonucleic acid (RNA) having complementary sequence, may be immobilized on the optical interference layer. In another example, metal organic compounds such as Cu-BTC (Copper Benzene-1,3,5-tricarboxylate), HKUST-1 (Copper Benzene-1,3,5-tricarboxylate), and UiO-66 ($[Zr_6O_4(OH)_4]$ clusters with 1,4-benzodicarboxylic acid), may be provided onto the optical interference layer to detect water, ethanol and acetone, respectively.

The sample segments can be arranged in any suitable configuration that can increase interaction between the sample segments and the analytes. The plurality of sample segments can be arranged in a two dimensional array. For example, the sample segments can be arranged in an array of 2×2, 3×3, 4×4, 5×5, 10×10, 20×20, or more. The number of sample segments formed on the surface of the optical interference substrate is not limited and can be any number depending on the number of analytes to be detected and the sensitivity of detection. For example, when there are more analytes to be detected, the number of sample segments will be higher in order to accommodate detection of at least one analyte per sample segment. In another example, by increasing the number of sample segments in the array for each target analyte, or by increasing the sample segment density, it is possible to detect the target analyte with higher precision due to the ability to have multiple measurements for the same target analyte. The segmentation of the optical interference layer to form the plurality of sample segments and the surface treatment, can be performed using a printer. Examples of suitable printers include an ink printer, impact dot matrix printer, sublimation printer, ink-jet printer, polymer printer for 3D-printing, or any combination thereof. In some examples, the printer is an ink-jet printer. The printer can be used to apply different types of surface treatment agents onto the respective sample segments, thereby treating the surfaces of the sample segments with different surface treatment agents.

The resolution of the printer can be compatible with the size of the sample segments to be formed by the printer. For example, the printer may have a resolution of about 144 by 144 dpi to about 9600 by 2600 dpi. In some examples, the printer may have a resolution of about 5760 by 1440 dpi to about 9600 by 2600 dpi. In some examples, the resolution of printer can be such that sample segments of dimensions of about 3 μm to about 100 μm or other sizes can be formed. In some examples, a printer with resolutions of 9600×2600 dpi or 5760×1440 dpi, which correspond to about 3 μm to 17 μm sized sample segments, can be suitable. These resolutions can be used for surface treatment of 50 μm² sensor units. In this case, assuming a 1 cm² substrate surface, it is possible to form an array of up to about 2,000,000 sample segments.

Various suitable image detectors can be used in the detection system described herein. The image detector is not particularly limited and can be any detector capable of detecting the interference spectrum. For example, the image detector can be a charged coupled device (CCD) camera. In another example, the image detector can be a photodiode array detector. In another example, the image detector can be a CMOS image sensor.

The CCD camera may have a resolution that can capture images of the interference spectrum at a resolution effective to recognize characteristics of the interference spectrum. For example, the CCD camera may have a resolution of at least about 0.3 million pixels. In a further example, the CCD camera may have a resolution of at least about 1 million pixels. Suitable resolutions for the CCD camera may include about 0.3 million pixels, about 0.5 million pixels, about 0.8 million pixels, about 1 million pixels, about 2 million pixels, about 3 million pixels, about 4 million pixels, about 5 million pixels, or a resolution between any of these values.

The detection system described herein can further include a computer configured to analyze the interference spectrum.

Figure 1:
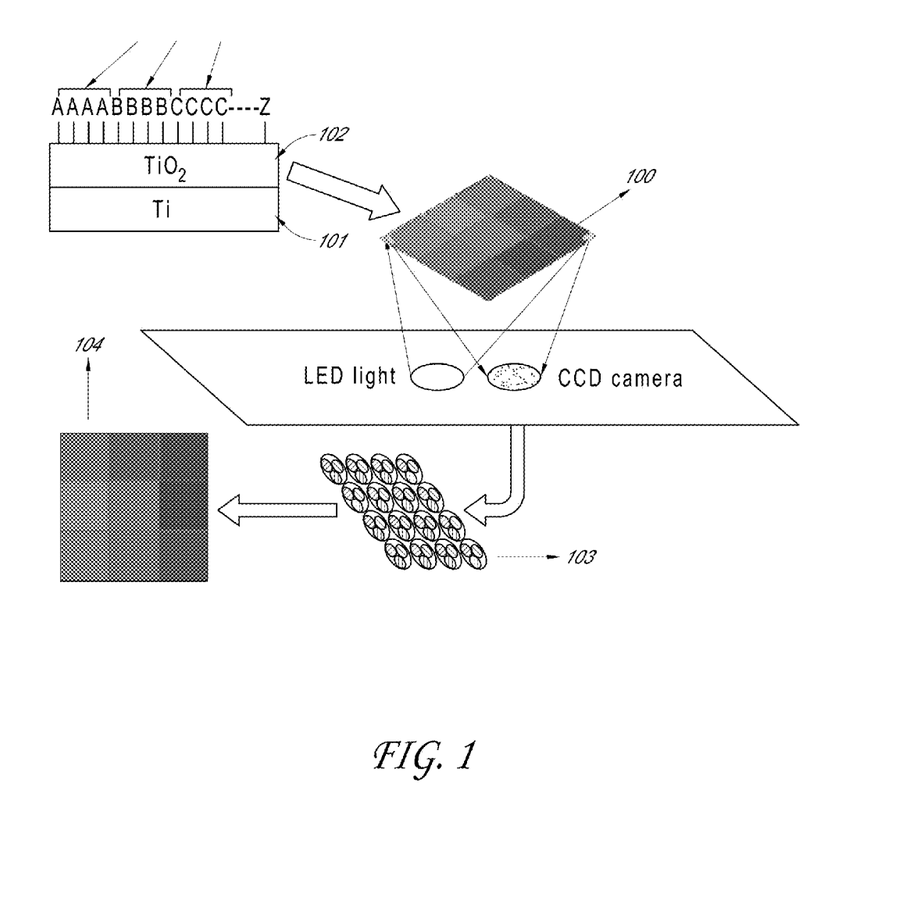
FIG. 1 shows a non-limiting example of a reflectometric interference spectroscopy (RIfS) detection system.

FIG. 1 shows an example schematic illustration of a reflectometric interference spectroscopy detection system. The detection system may include a two-dimensional array of surface treated sample segments 100. The sample segments 100 can be arranged in a configuration as described above, for example in a 3×3 configuration on a surface of the optical interference layer. Each of the sample segments in the array may have surfaces that have undergone different types of surface treatment. The different types of treatment to the surfaces can be carried out using a printer as described above, for example an ink-jet printer. The substrate may be metallic or non-metallic as described above. For example, with reference to FIG. 1, the substrate can be a metallic material such as titanium 101. The substrate may include an optical interference layer at the surface portion as described above, and the optical interference layer can for example be titanium oxide ($TiO_2$) 102. Each of the surface treated sample segments can be configured to contact a sample suspected of containing different types of analytes, such that each analyte can be contacted (for example, adsorbed) on the respective sample segments configured to have greater selectivity and/or sensitivity to that analyte as shown in 103. When the sample segments are illuminated with the light source, optical interference occurs at each of the sample segments, forming an interference spectrum 104 at each of the sample segments that is characteristic of the analyte at the sample segment. The interference spectrum 104 can be detected by an image detector as described above, for example, a CCD camera. Where the image detector is the CCD camera, changes in intensity of light reflected from the sample segments for each color component (for example, Red, Blue and Green of the color spectrum) can be measured to quantify the amount of adsorbed analyte. Therefore, monitoring of the analyte amount in the sample or the thickness of the adsorbed analyte on the optical interference substrate can be achieved by monitoring the reflected light intensity for each color component.

The sensitivity and accuracy of detection can be improved by increasing the resolution of the image detector. For example, where an array of sample segments (for example, an array of 100 segments) is measured with a CCD camera having a high resolution (for example, about 10 million pixels), any change in adsorption thickness as indicated by characteristics of the interference spectrum for each sample segment can be recognized based on an average of about 100,000 pixels per sample segment, thereby providing a high signal to noise ratio for the detection system. The detection system described herein can allow the formation of an array structure, including a large number of highly diverse sample segments for detecting different analytes on a substrate at low costs.

The sensitivity and accuracy of detection can also be improved by configuring surfaces of the optical interference layer to facilitate adsorption of the analytes onto the sample segments. For example, projections and recesses can be formed on the surface of the optical interference layer to increase the surface area, thereby providing a larger contact surface for adsorption of the analytes. In a further example, a porous optical interference layer as described above (for example, a porous titanium oxide optical interference layer) can be formed on an underlying substrate material (for example, titanium metal substrate) instead of a smooth optical interference layer, in order to increase surface area of contact with the analytes and thus sensitivity of the detection.

Method of Detecting Analytes

The detection system as described herein can have applications as chemical sensors and biosensors.

The method of detecting two or more analytes in a sample can include providing a sample suspected of containing two or more analytes to be detected, and contacting the sample with at least one sensor. The sensor may include a substrate, and an optical interference layer on the substrate. The optical interference layer may include a plurality of sample segments, wherein two or more of the plurality of sample segments are configured to have different affinities to the two or more analytes. The method may further include illuminating the two or more of the plurality of sample segments with at least one light source, and detecting an interference spectrum from each of the two or more of the plurality of sample segments, thereby detecting the two or more analytes in the sample.

The detection method may further include comparing the interference spectrums from at least one of the plurality of sample segments with a reference interference spectrum.

Various types of reference interference spectrums may be suitable. In some examples, the reference interference spectrum can be measured from the sample segment before the sample is contacted with the sample segment. In some examples, the reference interference spectrum is measured from a reference optical interference layer.

Comparing the interference spectrum of the sample segment with the reference interference spectrum can help to determine the concentration of at least one of the two or more analytes in the sample. Comparing the interference spectrum of the sample segment with the reference interference spectrum can also help to identify at least one of the two or more analytes in the sample.

In some examples, the comparing step can further include comparing changes in reflectance of the interference spectrum at one or more selected wavelengths. In some examples, the comparing step may further include comparing changes in differential frequency of the interference spectrum in one or more selected wavelengths. The one or more selected wavelengths can be about 620 nm to about 740 nm. In some examples, the one or more selected wavelengths can be about 450 nm to about 495 nm. In some examples, the one or more selected wavelengths can be about 520 nm to about 570 nm. Further examples of suitable wavelengths include: about 620 nm, about 660 nm, about 680 nm, about 700 nm, about 720 nm about 740 nm, or a wavelength between any of these values.

The detection method described herein may further include testing one or more positive control samples. The detection method described herein may also include testing one or more negative control samples. The detection method described herein may also further include testing one or more known samples to generate a calibration curve.

Suitable analytes that can be detected by the detection method described herein may include those as described above. The analytes may be present in a gaseous sample or in a liquid sample.

The detection method as described herein may further include performing analysis of the interference spectrum using a computer.

The optical interference layer may include at least one metal oxide as described above, for example, titanium oxide ($TiO_2$). The optical interference layer may have a smooth surface or may be porous, as described above.

The light source may include those as described above, for example, a broadband light source, or a light source configured to emit ultraviolet light, visible light, infrared light, or any combination thereof.

The optical interference substrate may include a metallic material or a non-metallic material. Suitable metallic materials and non-metallic materials include those as described above. For example, the optical interference substrate may include a metallic material such as titanium.

The interference spectrum may be detected using an image detector. Suitable image detectors include those as described above, for example, a CCD camera. The CCD camera may have a resolution as described above, for example, at least about 1 million pixels.

Method of Making a Sensor

A method of making a sensor can include forming an optical interference layer on a substrate, segmenting the optical interference layer into a plurality of sample segments, and configuring two or more of the plurality of sample segments to have different affinities to two or more analytes.

The segmenting of the optical interference layer may include printing a pattern on a surface of the optical interference layer to define the plurality of sample segments. The pattern can define a grid array, for example, a two-dimensional array. The printing can be performed using a printer such as an ink printer, impact dot matrix printer, sublimation printer, ink-jet printer, polymer printer for 3D-printing, or any combination thereof.

The printer may have a resolution suitable for forming the sample segments. For example, the printer may have a resolution of about 144 by 144 dpi to about 9600 by 2600 dpi. In some examples, the printer may have a resolution of about 5760 by 1440 dpi to about 9600 by 2600 dpi.

In some examples, the forming of the optical interference layer on the substrate may include vacuum deposition, sputtering, casting, reprecipitation, recrystallization, spin coating, dipping, layer-by-layer method, graft polymerization, or any combination thereof. In some examples, the forming of the optical interference layer may include forming a layer of metallic material on the substrate, and oxidizing the layer of metallic material. For example, the metallic material may be as described above such as titanium, and the optical interference layer may be titanium oxide ($TiO_2$) after the oxidation. The oxidizing step may include anodic oxidation of the metallic material in the presence of at least one electrolyte. The electrolyte can for example be aqueous sodium hydroxide, where a smooth optical interference layer is desired. The electrolyte can for example be a solution of ethylene glycol and ammonium fluoride, where a porous optical interference layer is desired. The optical interference layer may also be formed by modifying a surface portion of the substrate. For example, where the substrate is a metallic material, its surface portion may be oxidized to form the optical interference layer. The forming of the optical interference layer may alternatively include forming a layer of non-metallic material such as a polymeric material on the substrate. The optical interference layer may be a smooth layer or may be porous as described above.

The configuring of the two or more of the plurality of sample segments to have different affinities to two or more analytes, may include contacting each sample segment with a surface treatment agent, wherein the surface treatment agent is a carboxylic acid, a phosphoric acid, a bio-polymer, a synthetic polymer, a metal organic compound, or any combination thereof. The choice of surface treatment agents can be dependent on the analytes to be detected, as have been described above.

EXAMPLES

Additional embodiments are disclosed in further detail in the following examples, which are not in any way intended to limit the scope of the claims.

Example 1—Detection System

An exemplary detection system for detecting three different analytes simultaneously is described herein. The detection system includes a sensor having a substrate and an optical interference layer on the substrate. The optical interference layer may have 9 sample segments arranged in a 3 by 3 array. The substrate can be a titanium plate, and the optical interference layer can be titanium dioxide ($TiO_2$). The optical interference layer may be formed by anodic oxidation of a surface portion of the titanium plate substrate in an electrolyte containing ethylene glycol, ammonium fluoride and water. The amount of ammonium fluoride in the ethylene glycol may be 0.006 g/ml, and the amount of water in the ethylene glycol may be 0.03 ml/ml. The anodic oxidation may be carried out at 20V for 40 minutes. The surface of the optical interference layer is expected to be porous after the anodic oxidization.

The optical interference layer may be defined into the 3 by 3 array by printing (with an inject printer) the sample segments on a surface of the optical interference layer. The sample segments may be assigned into 3 groups, each group having 3 sample segments. A first group of sample segments is intended for detecting humidity. A second group of sample segments is intended for detecting ethanol. A third group of sample segments is intended for detecting acetone.

In order to configure the 3 groups of sample segments to have different affinities for the 3 analytes, different surface treatment agents can be applied to the 3 groups of sample segments. For example, three types of metal organic compounds can be applied onto the optical interference later to detect water, ethanol and acetone. One or more thin layers of Cu-BTC (Copper Benzene-1,3,5-tricarboxylate) can be applied onto the optical interference layer to detect acetone; one or more thin layers of HKUST-1 (Copper Benzene-1,3,5-tricarboxylate) can be applied onto the optical interference layer to detect ethanol; and one or more thin layers of UiO-66 ($[Zr_6O_4(OH)_4]$ clusters with 1,4-benzodicarboxylic acid) can be applied onto the optical interference layer to detect water as an analyte.

The detection system may further include a white light source, and a CCD image detector. The sensor may be contacted with a sample suspected of containing the 3 analytes, and each of the 3 analytes selectively adsorbs onto the respective sample segments. The white light from the light source irradiates the sample segments, and reflected light from each sample segment interferes at the surface to form an interference spectrum. The interference spectra from the 3 groups of sample segments are expected to exhibit different characteristics. The interference spectra can be detected by the CCD image detector.

For each group of sample segments, the interference spectrum is observed before and after analyte adsorption. Changes in characteristics of the interference spectrum can be measured by comparing changes in reflectance or intensity of the reflected light at different wavelengths such as in the red (640 nm), blue (470 nm) and green (520 nm) wavelengths of the visible light spectrum. The change in the light intensity at the specific wavelengths can be converted to optical thickness change using known theories of geometric optics. From the optical thickness change, the adsorption amount of the analyte can be estimated.

Changes in characteristics of the interference spectrum can also be measured by comparing the change in number of pixels of red, blue and green color components before and after analyte adsorption. The change in the number of pixels can be correlated (using known theories of geometric optics) to the amount of analyte adsorbed onto the sample segment.

The detection system as described in this Example can advantageously allow simultaneous detection of multiple analytes.

Example 2—Formation of Smooth and Porous Optical Interference Layers

Figure 2A:
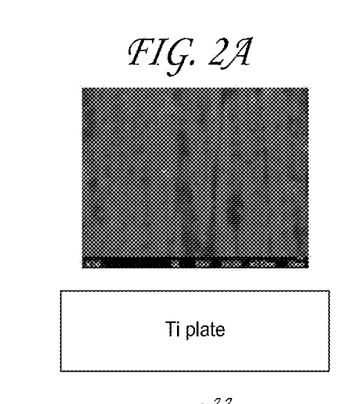
FIG. 2A shows a titanium metal substrate and an image of its surface before anodic oxidation.

Two gas sensors for comparing acetone adsorption on different optical interference surfaces in Example 3 were fabricated. One gas sensor had a porous titanium dioxide optical interference layer on a titanium substrate. The other gas sensor had a smooth titanium dioxide optical interference layer on a titanium substrate. The porous and smooth titanium optical interference layers were each formed by anodic oxidation of a surface portion of their respective titanium substrate. FIG. 2A shows the titanium substrate before the anodic oxidation, and an image of the substrate surface.

Figure 2B:
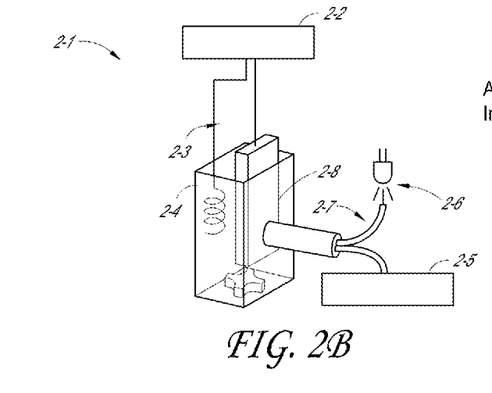
FIG. 2B shows an equipment set-up for performing anodic oxidation of a surface of the titanium metal substrate.

FIG. 2B shows an experimental set-up 2-1 that was used to perform the anodic oxidation of the titanium substrate surface. The reaction set-up 2-1 included an electric source meter 2-2, a platinum wire 2-3 for connecting the electric source 2-2 with an electrolyte 2-4. The electric source 2-2 provided a voltage of 0 to 60 volts. The titanium substrate 2-8 was immersed in the electrolyte during anodic oxidation. The surface morphology of the titanium substrate before and after anodic oxidation in different electrolytes were imaged by spectrometer 2-5 in the presence of white LED light source 2-6. The optical fiber 2-7 connected spectrometer 2-5 and the LED light source 2-6 as shown in FIG. 2B.

Figure 2C:
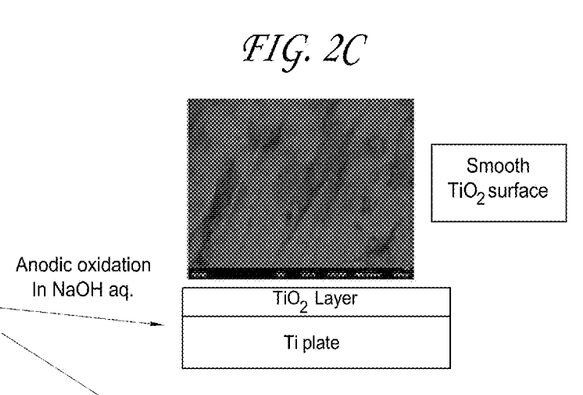
FIG. 2C shows a titanium metal substrate having a smooth titanium oxide optical interference layer, and an image of the smooth surface.
Figure 2D:
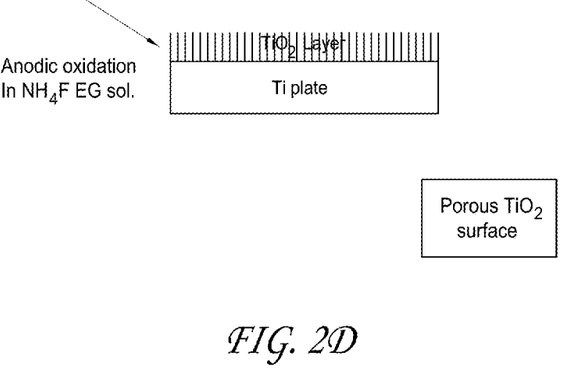
FIG. 2D shows a titanium metal substrate having a porous titanium oxide optical interference layer, and an image of the porous surface.

In the fabricating of the porous titanium dioxide optical interference layer on the titanium substrate, the surface portion of the titanium substrate was subjected to anodic oxidation in an electrolyte containing 10 ml ethylene glycol, 0.06 g ammonium fluoride and 0.3 ml water. The anodic oxidation was carried out at 20 V for 40 minutes. FIG. 2D shows the porous titanium dioxide layer on the titanium substrate, and an image of the surface of the porous titanium dioxide layer.

In the fabricating of the smooth titanium dioxide optical interference layer, the surface portion of the titanium substrate was subjected to anodic oxidation in 100 mM of sodium hydroxide aqueous solution. The anodic oxidation was carried out at 20 V for 40 minutes. FIG. 2C shows the smooth titanium dioxide layer on the titanium substrate, and an image of the surface of the smooth titanium dioxide layer.

As can be seen from FIGS. 2C and 2D, anodic oxidation in the presence of difference electrolytes can result in different surface morphologies.

Example 3—Acetone Adsorption on Smooth and Porous Optical Interference Surfaces

Acetone adsorption behavior was observed on the two gas sensors from Example 2. Each gas sensor was exposed to a gaseous sample of acetone and the acetone adsorbed surface of the optical interference layer was illuminated with while light.

Figure 3A:
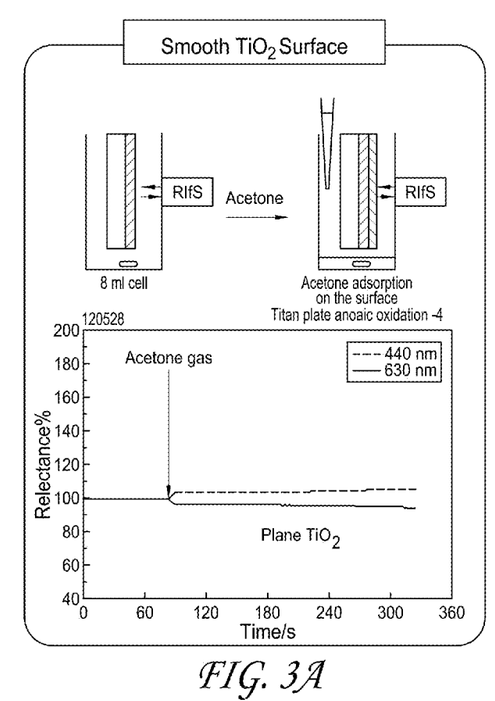
FIGS. 3A and 3B show non-limiting examples of changes in reflectance of an interference spectrum before and after adsorption of low-molecular-weight molecules (for example, acetone gas) on the optical interference layers of the optical interference substrates of FIG. 2C and FIG. 2D.

FIG. 3A shows a graph of reflectance vs. time for the interference spectrum formed before and after adsorption of acetone gas on the smooth titanium dioxide optical interference layer. As shown in FIG. 3A, when acetone was deposited on the smooth titanium dioxide surface, the interference spectrum shifted such that the intensity of reflected light at a longer wavelength (630 nm) decreased, while the intensity of reflected light in a shorter wavelength (440 nm) increased.

Figure 3B:
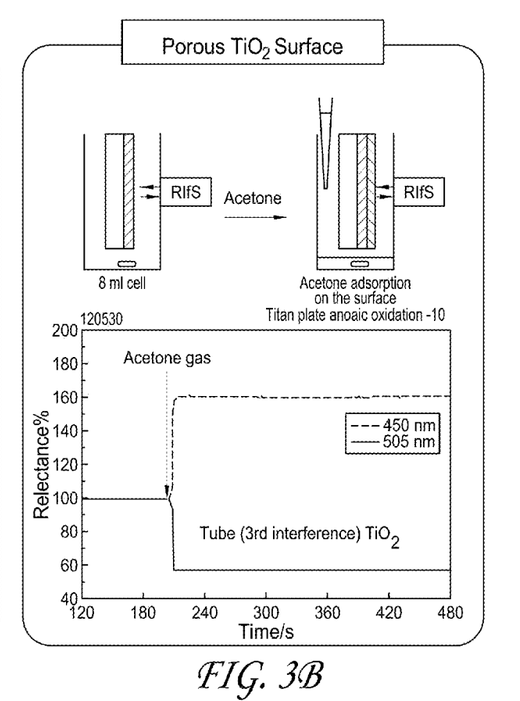

FIG. 3B shows a graph of reflectance vs. time for the interference spectrum formed before and after adsorption of acetone gas on the porous titanium dioxide optical interference layer. As shown in FIG. 3B, when acetone was deposited on the porous titanium dioxide surface, the interference spectrum shifted such that the intensity of reflected light at a longer wavelength (505 nm) decreased, while the intensity of reflected light in a shorter wavelength (450 nm) increased.

In comparing FIGS. 3A and 3B, it was observed that acetone adsorption on the porous optical interference layer exhibited reflectance changes that were significantly greater than the smooth optical interference layer. Therefore, by increasing surface area of the optical interference layer, for example, by having a porous surface or other forms of uneven surfaces, changes in reflectance of the interference spectrum can be amplified and sensitivity of the detection system can therefore be improved.

Example 4—Analyses of Interference Spectrum with a Photodiode Array

Figure 4A:
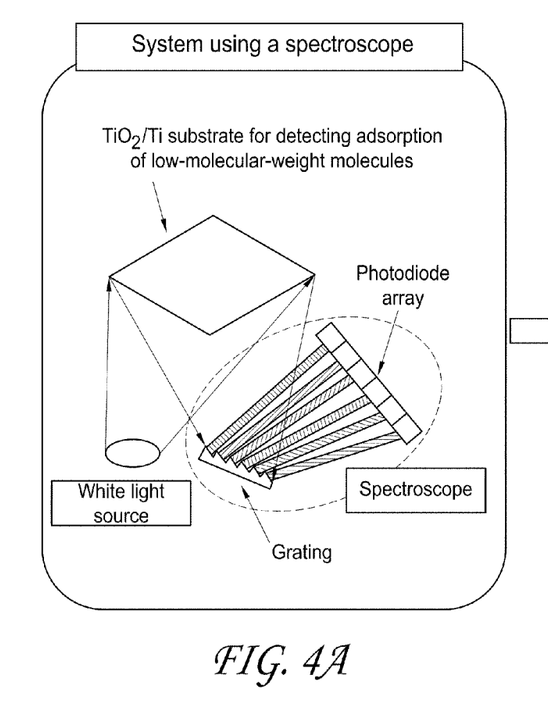
FIG. 4A shows a detection system having a photodiode array image detector.

FIG. 4A shows an exemplary set-up for detecting interference spectrum formed by reflected light from an optical interference surface with adsorbed analyte such as low molecular weight molecules. The detection system includes a white light source, a gas sensor having a titanium substrate and a thin film of titanium oxide formed on the titanium substrate, and a photodiode array image detector.

The adsorption thickness of the analyte can be determined by analyzing the interference spectrum at one or more wavelengths. Depending on the characteristics of the interference spectrum, an arbitrary combination of wavelengths may be selected and changes in reflectance at these wavelengths can be monitored before and after analyte adsorption. The changes in reflectance can be correlated with the thickness analyte adsorbed onto the optical interference surface.

Example 5—Analyses of Interference Spectrum with a Color Imaging Device

Figure 4B:
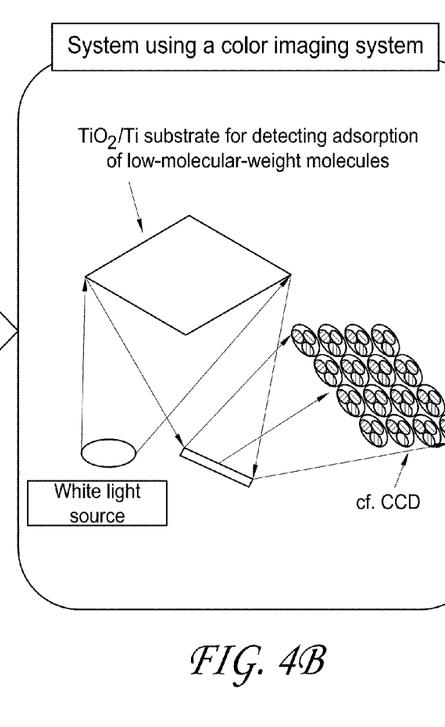
FIG. 4B shows a detection system having a charged coupled device (CCD) camera as the image detector.

FIG. 4B shows a detection system that was used to detect interference spectrum formed by reflected light from an optical interference surface with adsorbed ethanol. The detection system included a white light source, a gas sensor having a titanium substrate and a thin film of titanium oxide formed on the titanium substrate, and a charge coupled device (CCD) image detector.

The adsorption thickness of the analyte was determined by analyzing the interference spectrum at the red, blue and green portions of the spectrum. The changes in reflectance and changes in number of pixels for each color component were correlated with the thickness analyte adsorbed onto the optical interference surface.

Example 6—Interference Spectrum Generated by Optical Interference Layers of Different Thicknesses Two gas sensors with differing thicknesses of optical interference layers were fabricated in accordance with the method described in Example 2 for porous layers. Two titanium substrates were subjected to anodic oxidation in an electrolyte containing 10 ml ethylene glycol, 0.06 g ammonium fluoride and 0.3 ml water, to form porous titanium dioxide layer on the surface of the substrates. The duration of anodic oxidation was different for the two substrates—one was 40 minutes while the other was 330 minutes. The substrate that had the longer duration of anodic oxidation resulted in a thicker layer of porous titanium dioxide layer formed.

Figure 5A:
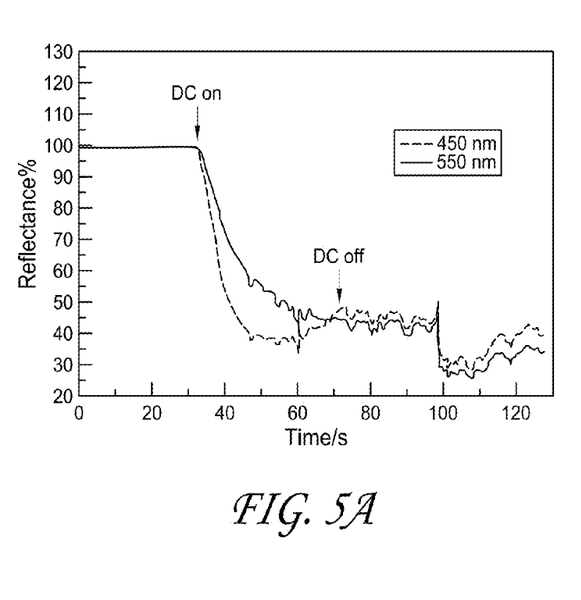
FIG. 5A shows changes in reflectance of reflected light (at wavelengths 450 nm and 550 nm) before and after the optical interference layer was formed on a titanium substrate by anodic oxidation. The anodic oxidation was carried out for about 40 minutes. The X-axis shows a time scale of the anodic oxidation. The Y-axis shows reflectance of the reflected light.
Figure 6A:
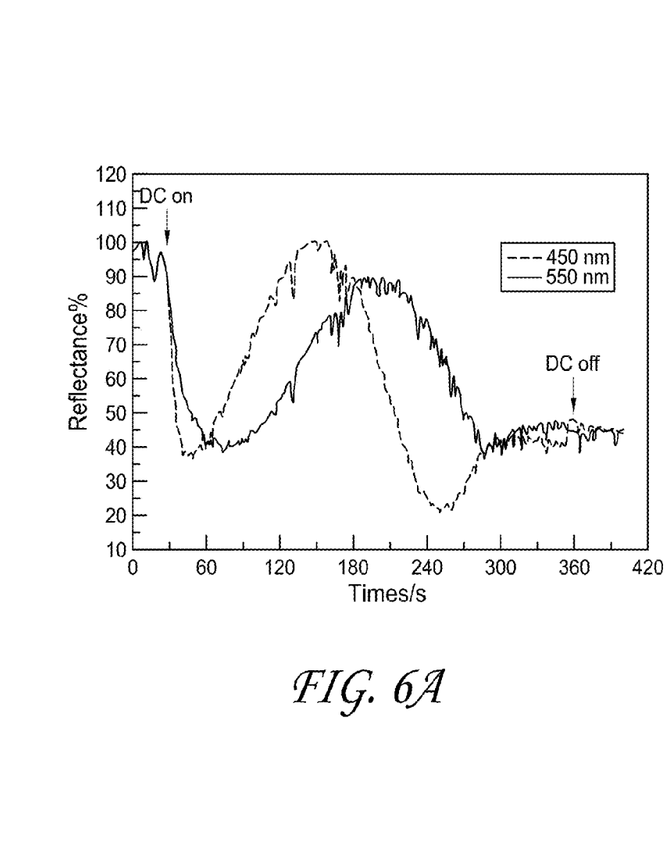
FIG. 6A shows changes in reflectance of reflected light (at wavelengths 450 nm and 550 nm) before and after the optical interference layer was formed on a titanium substrate by anodic oxidation. The anodic oxidation was carried out for about 330 minutes. The X-axis shows a time scale of the anodic oxidation. The Y-axis shows reflectance of the reflected light.

The titanium substrates were illuminated with white light and the interference spectrum form was monitored from the start to the end of the anodic oxidation. FIGS. 5A and 6A show the changes in reflectance of the interference spectrum at wavelengths 450 nm and 550 nm for the two substrates during the anodic oxidation. As can be seen from FIGS. 5A and 6A, reflectance of the interference spectrum at the shorter wavelength (450 nm) and at the longer wavelength (550 nm) are generally opposite from each other as the thickness of porous titanium dioxide layer increases (or as the duration of anodic oxidation increases). At any particular duration of oxidation or layer thickness, there is a characteristic combination of reflectance values for the two wavelengths, thus providing a form of reference for determining thickness of the porous titanium dioxide layer.

Figure 5B:
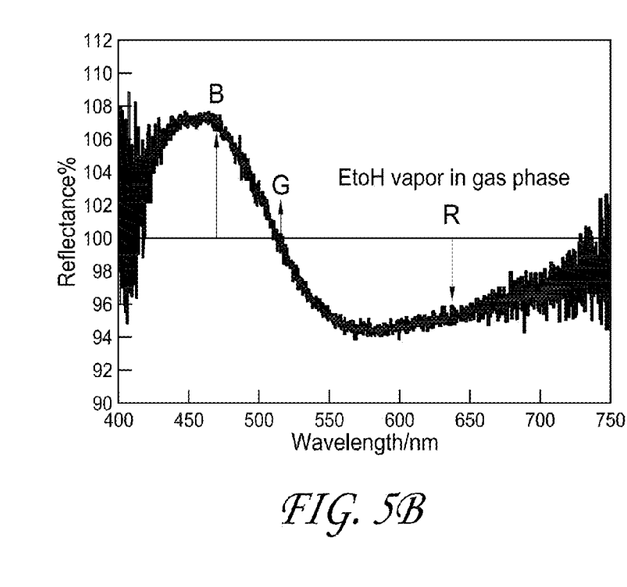
FIG. 5B shows changes in reflectance of reflected light from the optical interference layer after exposure to ethanol vapor. The X-axis shows wavelength of the reflected light. The Y-axis shows reflectance of the reflected light.
Figure 5C:
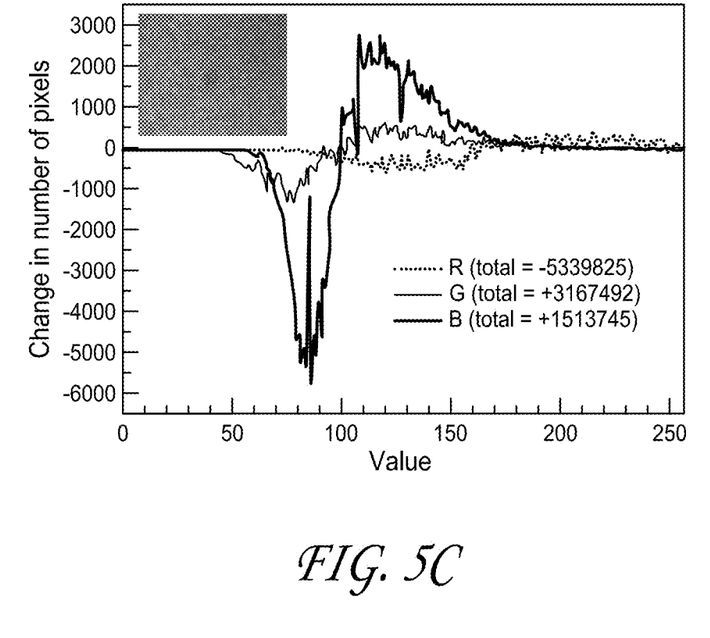
FIG. 5C shows changes in number of pixels of red, blue and green components of an imaged area of the optical interference layer before and after exposure to ethanol vapor. The X-axis represents a tonal scale of the image. The Y-axis shows the change in number of pixels after the exposure to ethanol vapor.
Figure 6B:
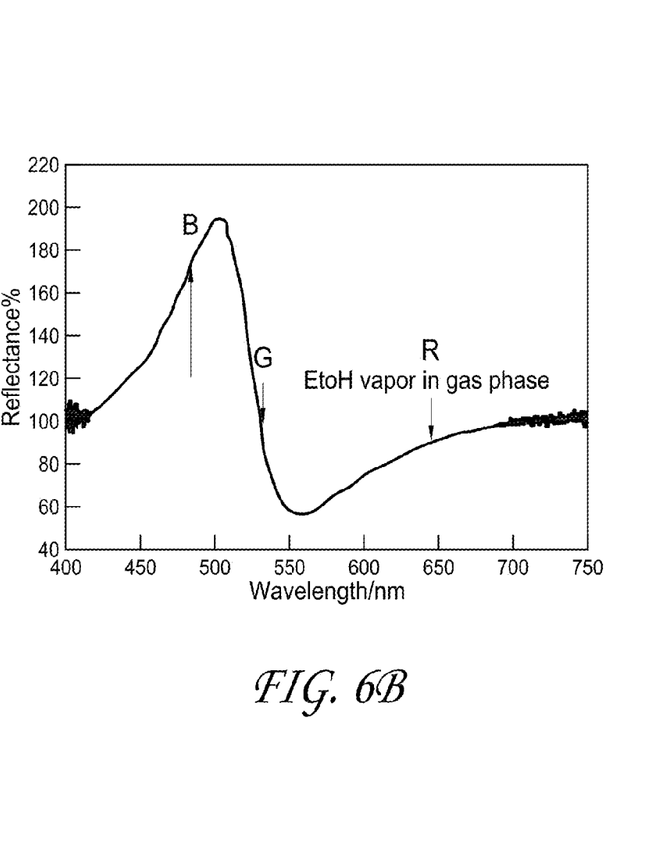
FIG. 6B shows changes in reflectance of reflected light from the optical interference layer after exposure to ethanol vapor. The X-axis shows wavelength of the reflected light. The Y-axis shows reflectance of the reflected light.
Figure 6C:
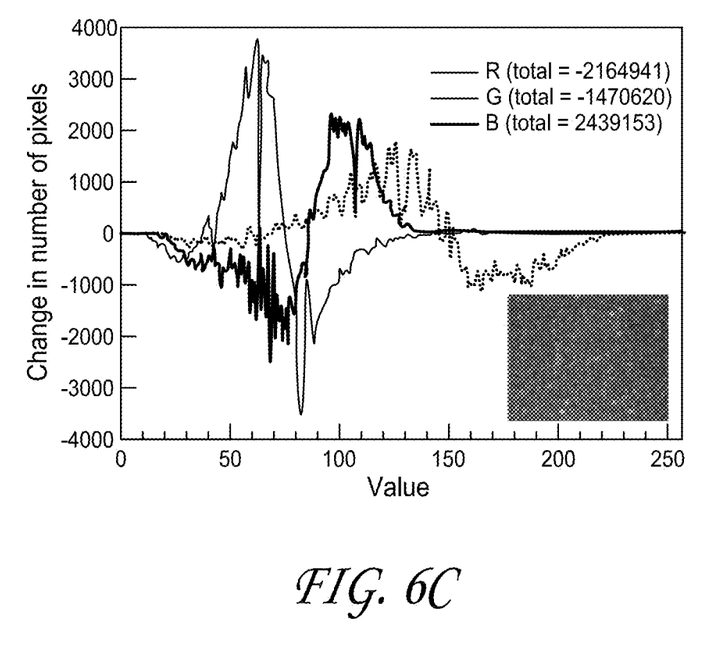
FIG. 6C shows changes in number of pixels of red, blue and green components of an imaged area of the optical interference layer before and after exposure to ethanol vapor. The X-axis represents a tonal scale of the image. The Y-axis shows the change in number of pixels after the exposure to ethanol vapor.

Each of the two gas sensors were immobilized on a base of a petri dish, and a color image of an arbitrary area was obtained by means of a CCD camera before analyte adsorption as shown in the embedded images of FIGS. 5C and 6C. Ethanol vapor was contacted with the porous titanium dioxide layer of each gas sensor for 10 seconds. The ethanol adsorbed optical interference surface was illuminated with the white light and the interference spectrum formed at the arbitrary area was detected by the CCD camera and subjected to color analysis.

FIG. 5B shows the changes in reflectance of reflected light (that forms the interference spectrum) from the optical interference layer (formed after 40 minutes of anodic oxidation of the substrate) after exposure to ethanol vapor. The changes in reflectance were monitored over a range of wavelengths. As can be seen from FIG. 5B, reflectance of reflected light in the blue and green bands increased, whereas the reflectance of reflected light in the red band decreased, after ethanol adsorption.

FIG. 5C shows the difference in number of pixels (Y-axis) for color components red, green and blue of the interference spectrum after ethanol adsorption vs. a tonal range (X-axis) of the spectrum. As can be seen from FIG. 5C, the number of blue pixels and green pixels with high intensities (high tonal range) increased and the number of blue pixels and green pixels with low intensities (low tonal range) decreased. On the other hand, the number of red pixels decreased in the intermediate and high intensity range. This is consistent with the observations in FIG. 5B, in which reflectance (or intensity) of reflected light in the blue and green bands increased, and the reflectance (or intensity) of reflected light in the red band decreased.

FIG. 6B shows the changes in reflectance of reflected light (that forms the interference spectrum) from the optical interference layer (formed after 330 minutes of anodic oxidation of the substrate) after exposure to ethanol vapor.

The changes in reflectance were monitored over a range of wavelengths. As can be seen from FIG. 6B, reflectance of reflected light in the blue band increased, whereas the reflectance of reflected light in the red and green bands decreased, after ethanol adsorption. The trend observed in FIG. 6B is different from FIG. 5B, which suggested that changes in thickness of the optical interference layer can influence the characteristics of the interference spectrum formed.

FIG. 6C shows the difference in number of pixels (Y-axis) for color components red, green and blue of the interference spectrum after ethanol adsorption vs. a tonal range (X-axis) of the spectrum. As can be seen from FIG. 6C, the number of blue pixels with high intensities (high tonal range) increased and the number of blue pixels with low intensities (low tonal range) decreased. On the other hand, the number of green pixels with high intensities (high tonal range) decreased and the number of green pixels with low intensities (low tonal range) increased. The number of red pixels increased in the intermediate range and decreased in the high intensity range. This is consistent with the observations in FIG. 6B, in which reflectance (or intensity) of reflected light in the blue band increased, and the reflectance (or intensity) of reflected light in the red and green bands decreased. The trend observed in FIG. 6C is also different from FIG. 5C, which reinforces the observation in FIGS. 5B and 6B that changes in thickness of the optical interference layer can influence the characteristics of the interference spectrum formed.

The Examples above demonstrated that simultaneous detection of multiple analytes is possible with the detection systems described herein. Sensitivity of detection can also be improved by increasing the surface area of the optical interference layer as can be seen in Example 3. The thickness of analyte adsorption (thus quantity of the analyte in a sample) can be determined by analysis of interference spectrum formed by the analyte adsorbed optical interference layer, such as by analyzing reflectance changes at various wavelengths of light, or changes in the number of pixels (where the CCD camera is the image detector) for various color components of the spectrum, before and after analyte adsorption.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," and so on). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, and others" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, and others" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, and so on). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, and others. As a non-limiting example, each range discussed herein can be readily broken down into a lower third, middle third and upper third, and others. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A detection system for detecting two or more analytes in a sample, the system comprising:
at least one sensor comprising:
a substrate; and
an optical interference layer on the substrate, the optical interference layer comprising a plurality of sample segments, wherein two or more of the plurality of sample segments are configured to have different affinities to two or more analytes in the sample, wherein the optical interference layer comprises $TiO_2$, $ZrO_2$, $HfO_2$, $Cr_2O_3$, or any combination thereof, and wherein the optical interference layer has a porous surface;
at least one light source configured to illuminate the two or more of the plurality of sample segments; and
at least one image detector configured to detect an interference spectrum from each of the two or more of the plurality of sample segments illuminated by the light source, thereby detecting the two or more analytes in the sample.

2. The detection system of claim 1, wherein the light source is configured to emit ultraviolet light, visible light, infrared light, or any combination thereof.

3. The detection system of claim 1, wherein the light source is a broadband light source.

4. The detection system of claim 1, wherein the substrate comprises a metallic material selected from titanium (Ti), silicon (Si), aluminum (Al), germanium (Ge), zirconium (Zr), hafnium (Hf), rutherfordium (Rf), chromium (Cr), molybdenum (Mo), tungsten (W), silver (Ag), gold (Au), and any combination thereof.

5. The detection system of claim 1, wherein the substrate comprises an organic material selected from a synthetic polymer, a biopolymer, a self-assembled monolayer (SAM), a bilayer membrane and any combination thereof.

6. The detection system of claim 1, wherein the substrate comprises an organometallic complex.

7. The detection system of claim 1, wherein the two or more analytes comprise a first analyte and a second analyte, and at least one of the plurality of sample segments has an affinity selective to the first analyte.

8. The detection system of claim 7, wherein at least another of the plurality of sample segments has an affinity selective to the second analyte.

9. The detection system of claim 1, wherein the optical interference layer comprises at least one metal oxide.

10. The detection system of claim 1, wherein the optical interference layer has a refractive index of equal to or more than 2.

11. The detection system of claim 1, wherein the plurality of sample segments is arranged in a two-dimensional array.

12. A method of detecting two or more analytes in a sample, the method comprising:
providing a sample suspected of containing two or more analytes to be detected;
contacting the sample with at least one sensor, the sensor comprising:
a substrate; and
an optical interference layer on the substrate, the optical interference layer comprising a plurality of sample segments, wherein two or more of the plurality of sample segments are configured to have different affinities to the two or more analytes wherein the optical interference layer comprises $TiO_2$, $ZrO_2$, $HfO_2$, $Cr_2O_3$, or any combination thereof, and wherein the optical interference layer has a porous surface;
illuminating the two or more of the plurality of sample segments with at least one light source; and
detecting an interference spectrum from each of the two or more of the plurality of sample segments, thereby detecting the two or more analytes in the sample.

13. The method of claim 12, further comprising comparing the interference spectrum from at least one of the plurality of sample segments with a reference interference spectrum.

14. The method of claim 13, wherein the comparing step determines a concentration of at least one of the two or more analytes in the sample.

15. The method of claim 13, wherein the comparing step identifies at least one of the two or more analytes in the sample.

16. The method of 13, wherein the comparing step further comprises comparing changes in reflectance of the interference spectrum at one or more selected wavelengths.

17. The method of 13, wherein the comparing step further comprises comparing changes in differential frequency of the interference spectrum at one or more selected wavelengths.

18. The method of claim 17, wherein the one or more selected wavelengths are about 620 nm to about 740 nm.

19. The method of claim 12, wherein at least one of the two or more analytes is a small molecule, a protein, a nucleic acid, an antibody, an antigen, a ligand, a DNA molecule, a RNA molecule, or any combination thereof.

20. The method of claim 12, wherein detecting the interference spectrum comprises detecting the interference spectrum with at least one image detector.

21. The detection system of claim 1, wherein each of the plurality of sample segments is surface treated with a surface treatment agent, and wherein the surface treatment agent is a carboxylic acid, a phosphoric acid, a bio-polymer, a synthetic polymer, or a metal organic compound.

* * * * *